US008702583B2

(12) United States Patent
Miller (10) Patent No.: US 8,702,583 B2
(45) Date of Patent: *Apr. 22, 2014

(54) ACTUATOR FOR A HEART ASSIST DEVICE (75) Inventor: Scott H Miller, Narrabeen (AU)

(73) Assignee: Sunshine Heart Company Pty, Ltd., Clontarf, NSW ( * ) Notice: Subject to any disclaimer, the term of this patent is extended or adjusted under 35 U.S.C. 154(b) by 138 days.

This patent is subject to a terminal disclaimer.

(21) Appl. No.: 13/111,499

(22) Filed: May 19, 2011

(65) Prior Publication Data

US 2011/0288367 A1 Nov. 24, 2011

Related U.S. Application Data (63) Continuation of application No. 10/595,605, filed as application No. PCT/AU2004/001487 on Oct. 28, 2004, now Pat. No. 7,955,248.

(30) Foreign Application Priority Data

Nov. 11, 2003 (AU) ................................ 2003906212

(51) Int. Cl.
 *A61N 1/362* (2006.01)
(52) U.S. Cl.
 USPC .......................................................... 600/18
(58) Field of Classification Search
 USPC ..................................... 600/16–18
 See application file for complete search history.

(56) References Cited

U.S. PATENT DOCUMENTS

| 283,660 A | 8/1883 | Reed |
| 929,571 A | 7/1909 | Dubied |
| 1,576,397 A | 7/1925 | Yanagi |
| 1,719,316 A | 7/1929 | Appleton |

(Continued)

FOREIGN PATENT DOCUMENTS

| AU | 2003277983 | 6/2008 |
| AU | 2003277983 B2 | 6/2008 |

(Continued)

OTHER PUBLICATIONS

Supplemental European Search Report issued in EP Application 00934813, mailed Oct. 19, 2006, 2 pages.

(Continued)

*Primary Examiner* — Christopher D Koharski
*Assistant Examiner* — Roland Dinga
(74) *Attorney, Agent, or Firm* — Davis, Brown, Koehn, Shors & Roberts, P.C.; Sean D. Solberg (57) ABSTRACT An actuator (10) for a heart assist device. The actuator (10) includes an inflatable balloon (12) and a shroud or wrap (14). The inflatable balloon (12) has a first body portion (22), a second body portion (26) and a flexure region joining (24) the first (22) and second (26) body portions. The shroud or wrap (14) is positioned adjacent the first body portion (24) and has a peripheral extent at least equal to the peripheral extent of the balloon flexure region (24). The balloon (12) and the shroud or wrap (14) are shaped such that the shroud or wrap (14) restrains a part of the balloon first body portion (22) at or near the flexure region (24) against displacement towards the shroud or wrap (outward displacement) past a predetermined limit but allows unrestrained displacement away from the shroud or wrap (inward displacement).

19 Claims, 9 Drawing Sheets (56) References Cited

U.S. PATENT DOCUMENTS

| | | |
|---|---|---|
| 3,467,077 A | 9/1969 | Cohen |
| 3,552,383 A | 1/1971 | Krueger et al. |
| 3,597,766 A | 8/1971 | Buck |
| 4,014,318 A | 3/1977 | Dockum et al. |
| 4,046,137 A | 9/1977 | Curless |
| 4,051,840 A | 10/1977 | Kantrowitz et al. |
| 4,176,411 A | 12/1979 | Runge |
| 4,195,623 A | 4/1980 | Zeff et al. |
| 4,236,482 A | 12/1980 | Gingerich et al. |
| 4,256,094 A | 3/1981 | Kapp |
| 4,277,706 A | 7/1981 | Isaacson |
| 4,304,225 A | 12/1981 | Freeman |
| 4,454,891 A | 6/1984 | Dreibelbis et al. |
| 4,457,673 A | 7/1984 | Conley et al. |
| 4,459,977 A | 7/1984 | Pizon et al. |
| 4,515,587 A | 5/1985 | Schiff |
| 4,583,523 A | 4/1986 | Kleinke et al. |
| 4,594,731 A | 6/1986 | Lewkowicz |
| 4,630,597 A * | 12/1986 | Kantrowitz et al. ............ 600/18 |
| 4,676,482 A | 6/1987 | Reece et al. |
| 4,697,574 A | 10/1987 | Karcher et al. |
| 4,763,646 A | 8/1988 | Lekholm |
| 4,771,765 A | 9/1988 | Choy et al. |
| 4,809,676 A | 3/1989 | Freeman |
| 4,813,952 A | 3/1989 | Khalafalla |
| 4,822,357 A | 4/1989 | Forster et al. |
| 4,881,939 A | 11/1989 | Newman |
| 4,886,490 A | 12/1989 | Shiber |
| 4,957,477 A | 9/1990 | Lundback |
| 4,979,936 A | 12/1990 | Stephenson et al. |
| 5,089,017 A | 2/1992 | Young et al. |
| 5,169,378 A | 12/1992 | Figuera |
| 5,197,980 A | 3/1993 | Gorahkov et al. |
| 5,205,810 A | 4/1993 | Guiraudon et al. |
| 5,222,980 A | 6/1993 | Gealow |
| 5,267,940 A | 12/1993 | Moulder |
| 5,273,518 A | 12/1993 | Lee |
| 5,290,249 A | 3/1994 | Foster et al. |
| 5,300,111 A | 4/1994 | Panton et al. |
| 5,337,752 A | 8/1994 | Reeves |
| 5,344,385 A | 9/1994 | Buck et al. |
| 5,360,445 A | 11/1994 | Goldowsky |
| 5,372,573 A | 12/1994 | Habib |
| 5,411,535 A | 5/1995 | Fujii et al. |
| 5,429,584 A | 7/1995 | Chiu |
| 5,447,523 A | 9/1995 | Schaldach |
| 5,453,076 A | 9/1995 | Kiyota et al. |
| 5,511,551 A | 4/1996 | Sano et al. |
| 5,554,177 A | 9/1996 | Kieval et al. |
| 5,568,544 A | 10/1996 | Keeler |
| 5,569,156 A | 10/1996 | Mussivand |
| 5,593,414 A | 1/1997 | Shipp et al. |
| 5,607,378 A | 3/1997 | Winston |
| 5,647,380 A | 7/1997 | Campbell et al. |
| 5,651,059 A | 7/1997 | Morgan et al. |
| 5,722,930 A | 3/1998 | Larson, Jr. et al. |
| 5,792,195 A | 8/1998 | Carlson et al. |
| 5,814,012 A | 9/1998 | Fleenor et al. |
| 5,820,542 A | 10/1998 | Dobak, III et al. |
| 5,827,171 A | 10/1998 | Dobak, III et al. |
| 5,833,655 A | 11/1998 | Freed et al. |
| 5,843,170 A | 12/1998 | Ahn |
| 5,876,434 A | 3/1999 | Flomenblit |
| 5,953,389 A | 9/1999 | Pruett et al. |
| 5,975,140 A | 11/1999 | Lin |
| 5,980,448 A | 11/1999 | Heilman et al. |
| 5,980,488 A | 11/1999 | Thorne |
| 6,030,336 A | 2/2000 | Franchi |
| 6,030,366 A | 2/2000 | Mitchell |
| 6,045,496 A | 4/2000 | Pacella et al. |
| 6,066,085 A | 5/2000 | Heilman et al. |
| 6,066,086 A | 5/2000 | Antaki |
| 6,118,776 A | 9/2000 | Berman |
| 6,132,363 A | 10/2000 | Freed et al. |
| 6,132,636 A | 10/2000 | Singh et al. |
| 6,146,325 A | 11/2000 | Lewis et al. |
| 6,210,318 B1 | 4/2001 | Lederman |
| 6,210,319 B1 | 4/2001 | Williams et al. |
| 6,226,843 B1 | 5/2001 | Crainich |
| 6,251,061 B1 | 6/2001 | Hastings et al. |
| 6,406,422 B1 | 6/2002 | Landesberg |
| 6,415,323 B1 | 7/2002 | McCanne |
| 6,432,039 B1 | 8/2002 | Wardle |
| 6,471,633 B1 * | 10/2002 | Freed ............................ 600/16 |
| 6,553,263 B1 | 4/2003 | Meadows et al. |
| 6,572,534 B1 | 6/2003 | Milbocker et al. |
| 6,585,635 B1 | 7/2003 | Aldrich |
| 6,604,140 B1 | 8/2003 | Beck |
| 6,616,596 B1 | 9/2003 | Milbocker |
| 6,626,821 B1 | 9/2003 | Kung et al. |
| 6,643,548 B1 | 11/2003 | Mai et al. |
| 6,792,308 B2 | 9/2004 | Corbucci |
| 6,808,483 B1 | 10/2004 | Ortiz et al. |
| 6,808,484 B1 | 10/2004 | Peters et al. |
| 6,984,201 B2 | 1/2006 | Khaghani et al. |
| 7,169,109 B2 | 1/2007 | Jansen et al. |
| 7,306,558 B2 | 12/2007 | Peters et al. |
| 7,347,811 B2 | 3/2008 | Peters et al. |
| 7,357,771 B2 | 4/2008 | Peters et al. |
| 7,360,558 B1 | 4/2008 | Chen et al. |
| 7,513,864 B2 | 4/2009 | Kantrowitz et al. |
| 7,740,575 B2 | 6/2010 | Peters et al. |
| 7,765,003 B2 | 7/2010 | Peters et al. |
| 7,887,478 B2 | 2/2011 | Peters |
| 8,002,691 B2 | 8/2011 | Peters et al. |
| 2001/0016676 A1 | 8/2001 | Williams et al. |
| 2003/0028599 A1 | 2/2003 | Kolsky |
| 2003/0105497 A1 | 6/2003 | Zhu et al. |
| 2004/0010180 A1 | 1/2004 | Scorvo |
| 2004/0073080 A1 | 4/2004 | Peters et al. |
| 2004/0097783 A1* | 5/2004 | Peters et al. ..................... 600/16 |
| 2004/0097784 A1* | 5/2004 | Peters et al. ..................... 600/18 |
| 2004/0147803 A1* | 7/2004 | Hegde et al. .................... 600/16 |
| 2004/0152945 A1* | 8/2004 | Kantrowitz et al. ............ 600/18 |
| 2004/0230090 A1 | 11/2004 | Hegde |
| 2006/0052866 A1 | 3/2006 | Gilles et al. |
| 2006/0135134 A1 | 6/2006 | Mezhvinsky et al. |
| 2007/0021830 A1 | 1/2007 | Peters |
| 2007/0093684 A1 | 4/2007 | Peters et al. |
| 2007/0129796 A1 | 6/2007 | Miller |
| 2007/0135677 A1 | 6/2007 | Miller et al. |
| 2007/0167898 A1 | 7/2007 | Peters et al. |
| 2007/0255350 A1 | 11/2007 | Torgerson |
| 2008/0027270 A1 | 1/2008 | Peters et al. |
| 2008/0139873 A1 | 6/2008 | Peters et al. |
| 2008/0161795 A1 | 7/2008 | Wang et al. |
| 2008/0167515 A1 | 7/2008 | Peters et al. |
| 2008/0194905 A1 | 8/2008 | Walsh |
| 2008/0266748 A1 | 10/2008 | Lee |
| 2008/0281412 A1* | 11/2008 | Smith et al. .................. 623/3.21 |
| 2009/0054949 A1 | 2/2009 | Alexander et al. |
| 2010/0016835 A1 | 1/2010 | Davey |
| 2010/0256440 A1 | 10/2010 | Maher |
| 2010/0292528 A1 | 11/2010 | De Plater |
| 2010/0292629 A1 | 11/2010 | Dacey, Jr. et al. |
| 2010/0324354 A1 | 12/2010 | Peters |
| 2011/0166630 A1 | 7/2011 | Phillips et al. |
| 2011/0196467 A1 | 8/2011 | Miller et al. |
| 2011/0270331 A1 | 11/2011 | Peters et al. |
| 2011/0275883 A1 | 11/2011 | Peters |
| 2011/0288367 A1 | 11/2011 | Miller |
| 2011/0298304 A1 | 12/2011 | Cotter |

FOREIGN PATENT DOCUMENTS

| | | |
|---|---|---|
| DE | 1541311 | 9/1969 |
| DE | 1541311 A1 | 9/1969 |
| EP | 0217964 | 4/1987 |
| EP | 0080348 B1 | 5/1988 |
| EP | 0080348 B2 | 5/1988 |
| EP | 0363203 | 4/1990 |
| EP | 0363203 A2 | 4/1990 |
| EP | 0364799 | 4/1990 |
| EP | 0216042 | 3/1991 |

(56) References Cited

FOREIGN PATENT DOCUMENTS

| | | |
|---|---|---|
| EP | 0216042 B1 | 3/1991 |
| EP | 0601804 | 6/1994 |
| EP | 0601804 A1 | 6/1994 |
| EP | 0364799 A2 | 5/1995 |
| EP | 0583012 | 7/1996 |
| EP | 0547733 | 4/1998 |
| EP | 1129736 | 9/2001 |
| EP | 1129736 A1 | 9/2001 |
| FR | 2458288 | 1/1981 |
| FR | 2458288 A1 | 1/1981 |
| FR | 2645739 | 10/1990 |
| FR | 2645739 A1 | 10/1990 |
| FR | 2767874 | 3/1999 |
| FR | 2767874 A1 | 3/1999 |
| GB | 2422114 | 4/2008 |
| GB | 2422114 B | 4/2008 |
| JP | 6510461 A | 11/1994 |
| JP | H6-510461 | 11/1994 |
| JP | 9-502376 | 3/1997 |
| JP | 9502376 A | 3/1997 |
| JP | 9-503933 | 4/1997 |
| JP | 9503933 A | 4/1997 |
| JP | 10-328297 | 12/1998 |
| JP | 10328297 A | 12/1998 |
| JP | 11285529 A | 10/1999 |
| JP | H11-285529 | 10/1999 |
| JP | 2000-000299 | 1/2000 |
| JP | 2000000299 A | 1/2000 |
| JP | 2000-510006 | 8/2000 |
| JP | 2000510006 T | 8/2000 |
| JP | 2001-276213 | 10/2001 |
| JP | 2001276213 A | 10/2001 |
| JP | 2003-135497 | 5/2003 |
| JP | 2003135497 A | 5/2003 |
| WO | WO 90/15630 | 12/1990 |
| WO | WO9015630 A1 | 12/1990 |
| WO | WO 92/08500 | 5/1992 |
| WO | WO9208500 A1 | 5/1992 |
| WO | WO 93/08874 | 5/1993 |
| WO | WO9308874 A1 | 5/1993 |
| WO | WO 95/05122 | 2/1995 |
| WO | WO9505122 A1 | 2/1995 |
| WO | WO 95/28127 | 10/1995 |
| WO | WO9528127 A1 | 10/1995 |
| WO | WO 97/40755 | 11/1997 |
| WO | WO9740755 A1 | 11/1997 |
| WO | WO 98/05289 | 2/1998 |
| WO | WO9805289 A1 | 2/1998 |
| WO | WO 98/14239 | 4/1998 |
| WO | WO9814239 A1 | 4/1998 |
| WO | WO 98/51367 | 11/1998 |
| WO | WO9851367 A1 | 11/1998 |
| WO | WO 99/02213 | 1/1999 |
| WO | WO9902213 A1 | 1/1999 |
| WO | WO 99/04833 | 2/1999 |
| WO | WO9904833 A1 | 2/1999 |
| WO | WO 99/45981 | 9/1999 |
| WO | WO9945981 A1 | 9/1999 |
| WO | WO 00/12168 | 3/2000 |
| WO | WO0012168 A1 | 3/2000 |
| WO | WO 00/76288 | 12/2000 |
| WO | WO0076288 A2 | 12/2000 |
| WO | WO 01/13974 | 3/2001 |
| WO | WO0113974 A2 | 3/2001 |
| WO | WO 01/83001 | 11/2001 |
| WO | WO0183001 A1 | 11/2001 |
| WO | WO 02/24254 | 3/2002 |
| WO | WO 02/24255 | 3/2002 |
| WO | WO0224254 A2 | 3/2002 |
| WO | WO0224255 A1 | 3/2002 |
| WO | WO 02/076305 | 10/2002 |
| WO | WO02076305 A1 | 10/2002 |
| WO | WO 03/011365 | 2/2003 |
| WO | WO03011365 A1 | 2/2003 |
| WO | WO 03/028787 | 4/2003 |
| WO | WO03028787 A1 | 4/2003 |
| WO | WO 2004/045677 | 6/2004 |
| WO | WO2004045677 A1 | 6/2004 |
| WO | WO 2005/041783 | 5/2005 |
| WO | WO 2005/042063 | 5/2005 |
| WO | WO 2005/042089 | 5/2005 |
| WO | WO 2005/044338 | 5/2005 |
| WO | WO 2008/053469 | 5/2005 |
| WO | WO2005041783 A1 | 5/2005 |
| WO | WO2005042063 A1 | 5/2005 |
| WO | WO2005044338 A1 | 5/2005 |
| WO | WO 2005/110512 | 11/2005 |
| WO | WO2005110512 A1 | 11/2005 |
| WO | WO2008053469 A2 | 5/2008 |
| WO | WO 2008/071223 | 6/2008 |
| WO | WO2008071223 A1 | 6/2008 |
| WO | WO 2011/098769 | 8/2011 |

OTHER PUBLICATIONS

Use of Heart Valve Sounds as Input to Cardiac Assist Devices, Research Disclosures, Mar. 1995.
Seymour Furman et al., "Cardiac Support by Periaortic Diastolic Augmentation", New York Journal of Medicine, Aug. 1, 1970, pp. 1964-1969.
J.L. Stewart, "Aortic Cuff a Cardiac Assistance Device", Polytechnic Institute of Brooklyn, 1968, pp. 9-108.
Hiroshi Odaguchi et al., "Experimental Study of Extraaortic Balloon Counterpulsation as a Bridge to Other Mechanical Assists" ASAIO Journal, pp. 190-194, vol. 42, No. 3, Lippincott Williams & Wilkins/ ASAIO, Hagerstown, MD, May 1, 1996.
"Use of Heart Valve Sounds as Input to Cardiac Assist Devices", Research Disclosures, Mar. 1995.
Luisada et al., On the Function of the Aortic Valve and the Mechanism of the First and Second Sounds, Japanese Heart Journal, vol. 18(1), Jan. 1977, pp. 81-91.
International Search Report issued in PCT/AU00/00654, mailed Aug. 18, 2000, 5 pages.
International Search Report issued in PCT/AU2002/000974, mailed Oct. 11, 2002, 5 pages.
International Preliminary Examination Report issued in PCT/AU2002/000974, completed Aug. 11, 2003, 8 pages.
International Search Report issued in PCT/AU2001/01187, mailed Nov. 5, 2001, 3 pages.
International Preliminary Examination Report issued in PCT/AU2001/01187, completed May 2, 2002, 4 pages.
International Search Report and Written Opinion issued in PCT/AU2007/001188, mailed Oct. 4, 2007, 12 pages.
International Preliminary Report on patentability, Chapter II, issued in PCT/AU2007/001188, completed Mar. 11, 2008, 8 pages.
International Search Report issued in PCT/AU2003/001450, mailed Feb. 2, 2004, 2 pages.
International Preliminary Examination Report issued in PCT/AU2003/001450, completed Mar. 2, 2005, 4 pages.
International Search Report issued in PCT/AU2003/001458, mailed Feb. 5, 2004, 5 pages.
International Prelminary Examination Report issued in PCT/AU2003/001458, completed Mar. 7, 2005, 7 pages.
International Search Report and Written Opinion issued in PCT/AU2004/001483, mailed Nov. 26, 2004, 5 pages.
International Search Report and Written Opinion issued in PCT/AU2004/001484, mailed Nov. 29, 2004, 5 pages.
International Search Report and Written Opinion issued in PCT/AU2004/01485, mailed Feb. 7, 2005, 6 pages.
International Search Report and Written Opinion issued in PCT/AU2004/001486, mailed Jan. 6, 2005, 7 pages.
International Search Report and Written Opinion issued in PCT/AU2004/01487, mailed Jan. 27, 2005, 12 pages.
International Search Report and Written Opinion issued in PCT/AU2004/01488, mailed Dec. 15, 2004, 6 pages.
Supplemental European Search Report issued in EP Application 00934813, mailed 0/19/2006, 2 pages.
Supplemental European Search Report issued in EP 01971489, completed Nov. 22, 2006, 4 pages.

(56) References Cited

OTHER PUBLICATIONS

Supplemental European Search Report issued in EP App No. 02748447, Feb. 6, 2007, 6 pages.
Supplemental European Search Report issued in EP App. No. 04789624, mailed Mar. 6, 2008, 7 pages.
Supplemental European Search Report issued in EP 04789625, mailed Nov. 18, 2009, 6 pages.
Office Action issued in JP Application No. 2004-552261, dated Mar. 2, 2010.
Office Action issued in JP Application No. 22006-53700, dispatched Jun. 22, 2010, with English translation, 12 pages.

* cited by examiner

ACTUATOR FOR A HEART ASSIST DEVICE

CROSS-REFERENCE TO RELATED APPLICATION

This application claims priority as a continuation of U.S. patent application Ser. No. 10/595,605, filed on Oct. 28, 2006, which is a National Stage of International PCT Application No. PCT/AU04/01487, filed on Oct. 28, 2004, which claims priority to Australia Patent Application No. 2003906212, filed on Nov. 11, 2003, all of which are hereby incorporated herein by reference in their entireties.

TECHNICAL FIELD

The present invention relates generally to heart assist devices, systems and methods and, more particularly, to an actuator for a counter-pulsation heart assist device.

BACKGROUND

U.S. Pat. No. 4,630,597 and International PCT Patent Application No. PCT/US00/22992 (WO 01/13974) both disclose heart assist devices that utilise an inflatable balloon that is positioned within an arterial vessel of a patient. The balloons replace a resected portion of the vessel and are cyclically inflated and deflated to expand into the vessel and thus assist in blood displacement during diastole and retract from within the vessel during systole.

Both of the above documents disclose devices that have a relatively rigid shell with an inlet/outlet port which is connected to a fluid pump. The flexible balloon seals around the periphery of the shell and extends back over the shell for some or all of its exterior. Another layer of material is then placed over the balloon exterior, adjacent the shell, to secure the balloon to the shell.

The Applicant's International PCT Patent Application No's. PCT/AU00/00654, PCT/AU01/01187, and PCT/AU02/00974 all disclose actuators that were found to fail due to fatigue in the balloon interfacing with the aorta.

It is an object of the present invention to provide an improved actuator.

SUMMARY

Accordingly, in a first aspect, the present invention provides an actuator for a heart assist device, the actuator including:

an inflatable balloon having a first body portion, a second body portion and a flexure region joining the first and second body portions; and a shroud or wrap adjacent the first body portion and having a peripheral extent at least equal to the peripheral extent of the balloon flexure region;

wherein the balloon and the shroud or wrap are shaped such that the shroud or wrap restrains a part of the balloon first body portion at or near the flexure region against displacement towards the shroud or wrap (outward displacement) past a predetermined limit but allows unrestrained displacement away from the shroud or wrap (inward displacement).

The balloon and the shroud are preferably shaped such that the shroud restrains said part of the balloon first body portion at or near the flexure region against outward displacement during inflation of the balloon but allows unrestrained inward displacement during deflation.

Preferably, during inward displacement, at least part of the inner surface of the balloon second body portion is able to be drawn against at least part of the inner surface of the balloon first body portion.

The shroud is preferably generally inwardly concave, most preferably elongated, and elliptical.

The first body portion, second body portion and flexure region are preferably integrally formed, most preferably by dip moulding.

The actuator preferably also includes a bushing adapted for connection to a motive power source.

The balloon preferably also includes a neck portion joined to the first portion, the neck portion being adapted for sealing connection with the bushing.

The shroud preferably also includes a neck portion adapted for sealing connection with the balloon neck portion.

In a second aspect, the present invention provides an actuator for a heart assist device, the actuator including:

a bushing adapted for connection to a hydraulic or pneumatic power source; and an inflatable balloon having a narrower neck portion adapted for sealing connection with the bushing exterior, wider first and second body portions and an arcuate flexure region joining the first and second body portions, the first body portion having a first end adjacent the neck portion and a second end adjacent the second body portion and being generally inwardly concave, the second body portion being inwardly concave when the balloon is inflated and generally outwardly concave when the balloon is deflated.

The device preferably also includes a shroud or wrap having a body portion with a peripheral extent at least equal to the peripheral extent of the balloon first and second body portions.

The balloon and the shroud or wrap are preferably shaped such that a part of the balloon first body portion at or near the flexure region is restrained against outward displacement past a predetermined limit by the shroud or wrap but unrestrained against inward displacement.

Preferably, during inward displacement, at least part of the inner surface of the balloon second body portion is able to be drawn directly against at least part of the inner surface of the balloon first body portion.

In a third aspect, the present invention provides a heart assist device including:

a hydraulic or pneumatic power source; and an actuator including:

a bushing adapted for operative connection to the motive power source;

an inflatable balloon having a narrower neck portion adapted for sealing connection with the bushing exterior, wider first and second body portions and a flexure region joining the first and second body portions, the first body portion having a first end adjacent the neck portion and a second end adjacent the second body portion and being generally inwardly concave, the second body portion being generally inwardly concave when the balloon is inflated and generally outwardly concave when the balloon is deflated; and a shroud or wrap having a body portion with a peripheral extent at least equal to the peripheral extent of the balloon first and second body portions, wherein the balloon and the shroud are shaped such that a part of the balloon first body portion at or near the flexure region is restrained against outward displacement by the shroud past a predetermined limit but unrestrained against inward displacement.

Preferably, during inward displacement, at least part of the inner surface of the balloon second body portion is able to be drawn against at least part of the inner surface of the balloon first body portion.

Preferably, the balloon and shroud are shaped such that substantially all of the balloon first body portion is restrained against outward displacement by the shroud and unrestrained against inward displacement.

In its preferred form, the heart assist device is configured for extra-aortic counter-pulsation. In this form, the balloon is positioned on the exterior of an arterial vessel.

In a further form, the heart assist device is configured for use either as an interposition graft in which the device replaces a completely resected section of the aorta or as an aortic patch in which an aperture is formed in the aorta which is filled with the device.

When the balloon is inflated, the flexure region preferably has a radius of curvature of at least 0.1 mm, more preferably a radius of curvature of approximately 1.0 mm and most preferably a radius of curvature of approximately 3.0 mm.

The ratio of the diameter of the balloon neck portion to the balloon flexure region is preferably no more than approximately 4:1, and more preferably approximately 3:1 and most preferably approximately 2:1.

The bushing preferably has an inlet/outlet bore. The bore preferably also includes one or more internal restrictions adapted to prevent suction of the balloon into the bore.

The balloon is preferably formed from silicone, polyurethane or a polyurethane-polysiloxane block co-polymer. The balloon is preferably formed by mandrel dipping. The balloon is preferably formed by dipping a suitably shaped mandrel into the polymer and allowing a thin coating of the polymer to cure on the mandrel. The balloon is preferably made of 2 to 4 coatings, with a total thickness of 150-300 microns. The balloon can then be removed from the mandrel.

The balloon neck portion is preferably a snug sealing fit over the bushing exterior. The shroud or wrap preferably has a neck portion that is a snug sealing fit over the balloon neck portion.

The bushing preferably has a slightly tapered neck portion adapted for engagement with the balloon neck portion. The bushing neck portion preferably has a converging taper in the direction of the balloon.

The balloon is preferably held in place on the aorta by a flexible wrap which extends about the aorta and bears against the first body portion of the balloon or a shroud mounted thereon. The wrap is preferably shaped to fit the second body portion of the balloon, and if desired also the neck portion. The wrap is preferably inelastic or slightly elastic so that its stretch and flexibility characteristics substantially match those of the native aorta.

In a fourth aspect, the present invention provides a flexible inflatable balloon for a blood displacing heart assist device, the balloon including:

a neck portion having first and second ends;

a substantially annular first body portion connected at its inner periphery to the neck portion second end; and a substantially oval or circular second body portion connected at its outer periphery to the outer periphery of the first body portion, the outer peripheries of the first and second body portions are connected along an annular inwardly concavely curved flexure portion adapted to maintain a radius of curvature during movement of the second body portion between inwardly concave and outwardly concave during deflation and inflation of the balloon respectively.

The balloon is advantageously formed as a single piece. This avoids the presence of a seam line as is disclosed in U.S. Pat. No. 4,630,597 or International patent specification WO 01/13974. Such seam lines have been found by the present inventors to raise stress levels in the balloon and reduce the operational life of the balloon.

A shroud can be provided to overlie and abut the annular first body portion of the balloon. The shroud is preferably shaped such that the shroud restrains said portion of the balloon at or near the flexure region against outward displacement during inflation of the balloon but allows unrestrained inward displacement during deflation. The shroud is preferably generally inwardly concave, most preferably elongated, and elliptical. The shroud preferably also includes a neck portion adapted for sealing connection with the balloon neck portion. The shroud may act to facilitate bonding a wrap to the first body portion of the balloon.

The balloon preferably also includes a bushing adapted for connection to a hydraulic or pneumatic power source. The bushing also acts to prevent inward collapse of the balloon neck portion during deflation. If desired the bushing can be formed with internal restrictions such as flutes, ribs or secondary lumens to prevent the balloon being sucked into the bushing during deflation of the balloon. The neck portion of the balloon is preferably adapted for sealing connection with the bushing. The bushing preferably has a taper adapting the relatively large diameter of the neck of the balloon to the relatively small diameter of a hydraulic or pneumatic fluid line connecting the balloon to a power source. This taper is preferably elongated to enhance the flexibility of the bushing along its central axis.

In a fifth aspect, the present invention provides an actuator for a heart assist device, the actuator including:

a flexible inflatable balloon having a neck portion connected at one end to a bulbous body portion having a first side and a second side; and a substantially inelastic shroud or wrap having a flared portion that extends over the adjacent first side of the balloon bulbous portion, wherein, during deflation, the second side of the bulbous body portion is able to be drawn against the first side of the bulbous body portion.

The shroud or wrap preferably supports the first side of the balloon bulbous portion against substantial movement whilst the second side of the balloon bulbous portion is free to move during inflation and deflation.

In a sixth aspect, the present invention provides a method of providing extra-aortic heart assistance using the actuator of the first or the second or the fifth aspect or the heart assist device according to the third aspect or the balloon of the fourth aspect, the method including mounting the balloon second body portion adjacent the exterior of an arterial vessel.

In a seventh aspect, the present invention provides a method of providing intra-aortic heart assistance using the actuator according to the first or the second or the fifth aspect or the heart assist device according to the third aspect, the method including resecting a portion of an arterial vessel and mounting the balloon with the balloon second body portion sealingly replacing the resected arterial portion.

BRIEF DESCRIPTION OF THE DRAWINGS

Preferred embodiments of the invention will now be described, by way of examples only, with reference to the accompanying drawings in which.

DETAILED DESCRIPTION

Figure 1:
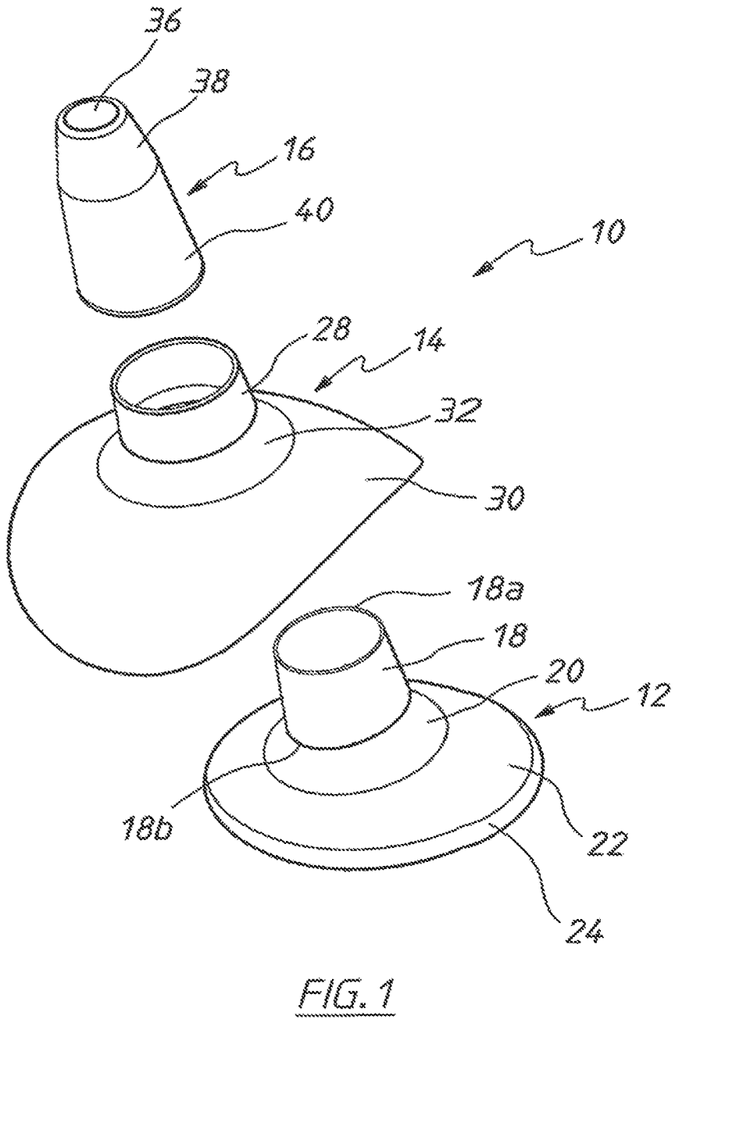
FIG. 1 is an exploded perspective view of a first embodiment of an actuator according to the invention.

FIG. 1 shows an exploded perspective view of an actuator 10 according to a first embodiment of the present invention, which is sized for pediatric use. The actuator 10 has a flexible, inflatable balloon 12, an inelastic shroud 14, and a relatively rigid bushing 16.

The balloon 12 is formed from Polyurethane or similar biocompatible and biostable material by mandrel dipping. The balloon 12 has a narrower neck portion 18 which is connected by a flared part 20 to a wider first body portion 22. A flexure region 24, which extends generally around the exterior of the balloon 12 at its widest part connects a second body portion 26 (see FIGS. 2 to 4) to the first body portion 22.

When viewed in plan, the first and second body portions are generally elliptical in shape and have a maximum width and length of about 20-35 mm and 50-90 mm respectively for adult sized balloons. The balloon neck portion has a diameter of approximately 10-14 mm at its distal end 18a and, at its proximal end 18b, it is elliptical in shape with dimensions of approximately 30-50 mm in the long axis and 15-30 mm in the short axis of the balloon 12, and with a converging taper therebetween. Pediatric balloons are also considered in this same application, but scaled downward appropriately.

The shroud 14 is formed, by mandrel dipping, from a material substantially equivalent to the material used for the balloon, such as a Polyurethane or a Polyurethane-Polysiloxane block co-polymer. The shroud 14 has a narrower neck portion 28 which is joined to a wider body portion 30 by a flared part 32. The shroud body portion 30 is also generally elliptical in shape when viewed in plan and has a larger peripheral extent (i.e. extends further in all directions) than the balloon body portions 22 and 26 and flexure region 24. More particularly, the shroud body portion 30 has a length (along the long axis of the balloon 12) of 60-100 mm and a minimum width of (across the short axis of the balloon 12) of 20 mm. The shroud neck portion 28 is sized to be a snug sealing fit over the exterior of the balloon neck portion 18.

The bushing 16 is formed, by injection moulding, from a flexible plastic such as Polyurethane or a similar material. The bushing 16 has a hollow bore 36 which is adapted for sealing connection with a fluid line from a motive power source such as a fluid pump (not shown). Suitable pumps are disclosed in the Applicant's International PCT Patent Application No. PCT/AU02/00974 entitled "A fluid pressure generating means", the contents of which are hereby incorporated by cross reference. The bushing 16 also has a relatively more tapered distal part 38 and a relatively less tapered proximal part 40. The proximal part 40 is sized to be a snug sealing fit within the interior of the balloon neck portion 18.

Figure 2:
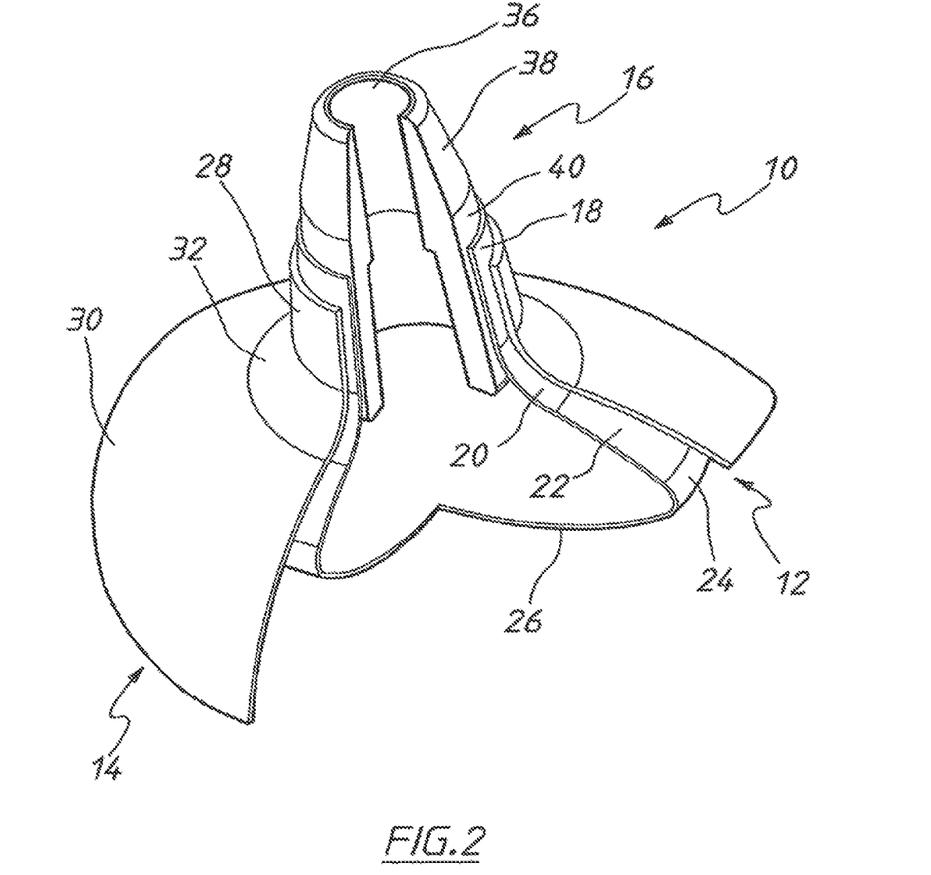
FIG. 2 is an assembled, partial cut away, perspective view of the actuator shown in FIG. 1.

FIG. 2 shows the device 10 after assembly. The assembly comprises initially stretching the neck portion 18 of the balloon 12 so that the proximal part 40 of the bushing 16 can be inserted therein. The balloon 12 is retained adjacent the bushing 16 by the shroud 14 being forced past the distal part 38 of the bushing 16 until it is a snug sealing fit on the exterior of the balloon neck portion 18 as shown. The bushing proximal part 40, the balloon neck portion 18, and the shroud neck portion 28 all have a common taper angle. The components are also bonded together with a suitable adhesive in order to ensure an effective seal therebetween.

Figure 3:
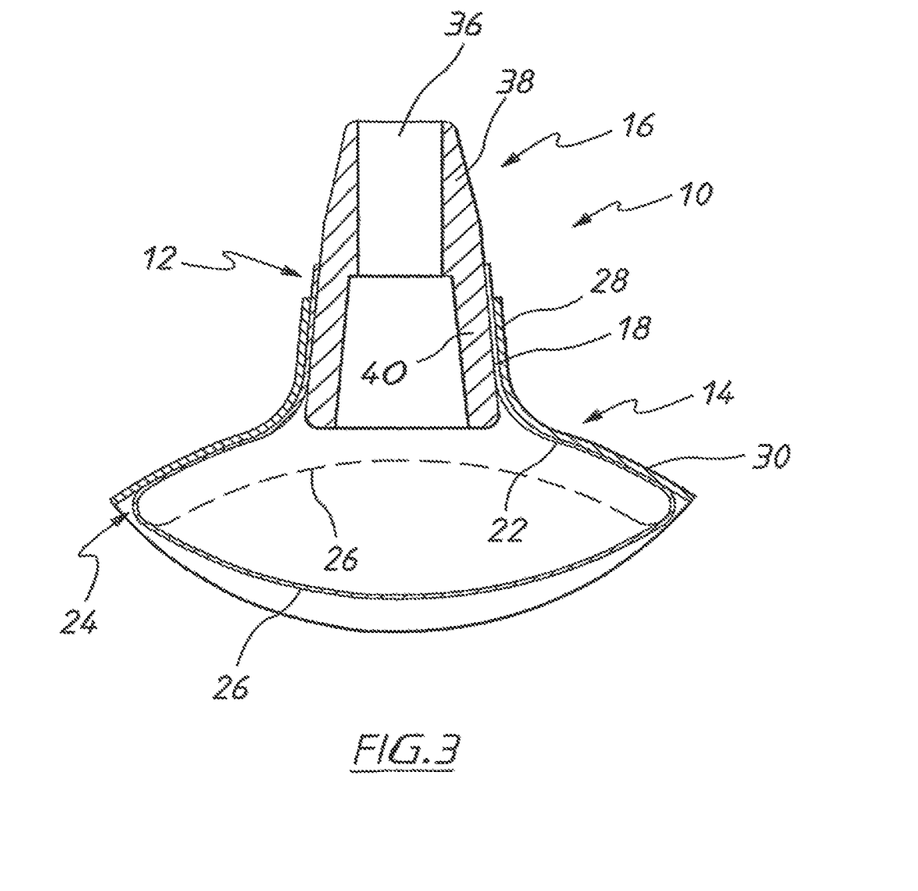
FIG. 3 is an assembled, cross sectional view of the actuator shown in FIG. 1 along the line 3-3.
Figure 4:
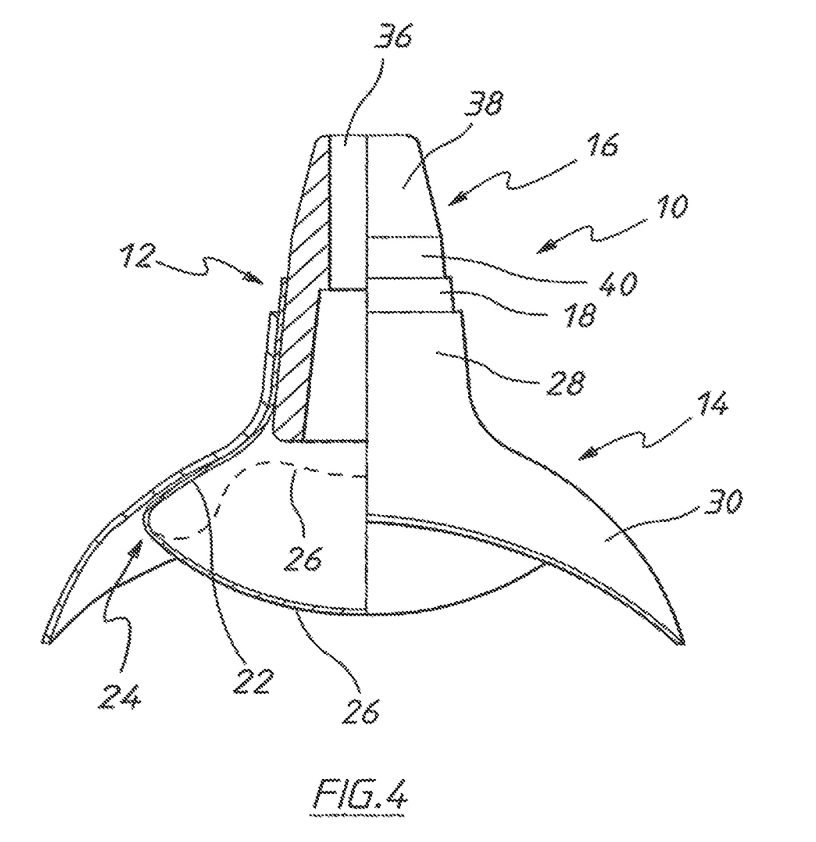
FIG. 4 is an assembled, cross sectional view of the actuator shown in FIG. 1 along the line 4-4.

The operation of the device 10 will now be described by with reference to FIGS. 3 and 4. FIG. 3 is a cross-sectional (anterior) view along the longitudinal direction of the aorta. FIG. 4 is a partial cross-sectional view orientated at 90 degrees from that of FIG. 3.

For extra-aortic heart assistance, the device 10 is placed with the balloon second portion 26 adjacent the exterior of an arterial vessel, most preferably the outer part of the ascending aorta (not shown). A flexible, relatively inelastic wrap is placed over the shroud 30 and around the aorta in order to retain the device 10 in place. Wraps are well known in the art and thus will not be described in further detail. The wrap can also be used in place of the shroud.

In use, fluid is cyclically driven to and from the balloon 12, via the bushing bore 36, to cyclically inflate and deflate the balloon 12. The inflated balloon 12 is shown in solid line in FIG. 3. The inflated balloon 12 compresses the aorta and thus assists in blood displacement during diastole. When the balloon 12 is deflated it retracts to the position shown in phantom line, which allows the aorta to return to its natural shape during systole.

As FIGS. 3 and 4 show, when the balloon 12 is inflated the shroud 14 restrains the balloon first portion 22, up to and including the part adjacent the flexure region 24, against outward displacement past a predetermined limit. That limit being defined by the shape of the shroud body portion 30. However, the shroud 14 does not restrain the inward displacement of the balloon first portion 22, particularly that part at or near the flexure region 24, during deflation. This allows the balloon 12 to always retain a relatively large radius of curvature (e.g. 1.0 mm) adjacent the flexure region 24, which is the part of the balloon 12 that undergoes the most deformation. This advantageously minimises stress and strain concentration in the flexure region 24, which results in a much more reliable and longer lasting balloon 18.

This is in contrast to the balloons shown in the two prior art documents mentioned previously which are restrained at a region equivalent to the flexure region for both inward and outward displacement. These balloons undergo a movement akin to pivoting or bending at their free edge. This results in high levels of stress concentration, and associated higher risk of failure, in those balloons.

Further, cycle testing of a group of actuators configured for use with sheep (and corresponding to the actuator 10 described above) were terminated after the equivalent of two years cycling without any failures. In addition, cycle testing of similar actuators configured for use with humans has achieved the equivalent of 18 months use without any failures.

The actuator 10 is also simpler, and thus cheaper, to assemble and manufacture than the prior art devices as the bushing 16 only engages with the balloon 12 in the region of their respective neck portions 40, 18, as opposed to positioning the bushing (or shell) more fully within the body portions of the balloon.

It should also be noted that the actuator 10 is designed to be applied to the outside of a blood vessel and is thus advantageously non-blood contacting as compared to the prior art devices discussed in the Background of the Invention, which are positioned within the wall of a blood vessel.

It should also be noted that the inward concavity of the balloon (when deflated) is designed to fit the arcuate ascending aorta particularly, to allow a conformal wrapping of the assembled actuator around the ascending aorta With balloon inflation, the aortic wall is displaced in a "thumbprinting" manner, which has been shown by finite element analysis to cause minimal strain concentration in the aortic wall and also to provide maximal blood volume displacement.

In a more preferred embodiment, the balloon has in its longitudinal plane, a gentle arc of the order of radius of 150-300 mm, to accommodate the slight spiral nature of the ascending aorta, to allow further conformal fitting of the assembled device.

Figure 5:
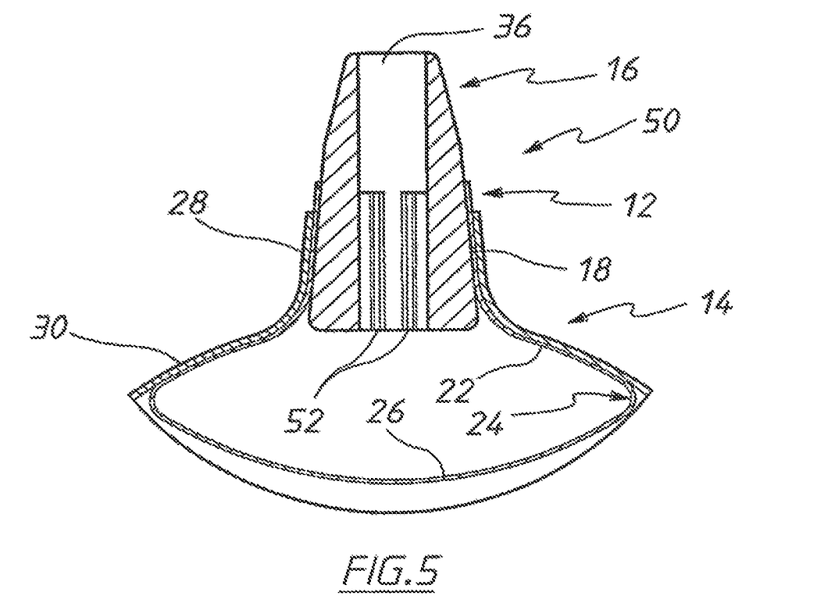
FIG. 5 is a cross sectional view of the second embodiment of an actuator according to the invention along the line 5-5.
Figure 6:
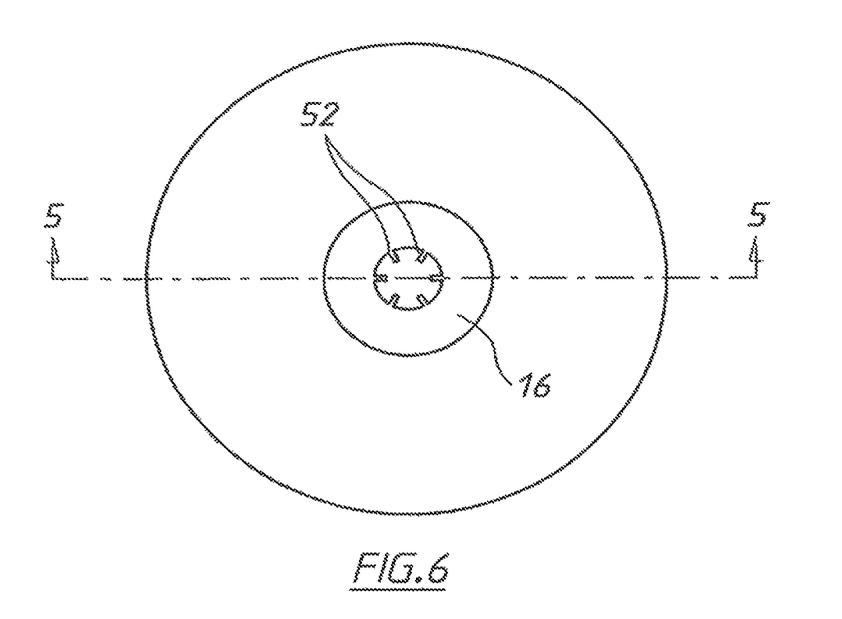
FIG. 6 is an underside view of the bushing used in the actuator shown in FIG. 5.

FIGS. 5 and 6 show a second embodiment of actuator 50 according to the invention. The device 50 is similar to the first embodiment and like reference numerals are used to indicate like features.

The major difference between the two embodiments is that the bushing 16 in the device 50 includes a series of internal projections 52 which serve to stop the balloon 18 being sucked into the bore 36 of the bushing during large amounts of suction/deflation. Such large amounts of suction/deflation can occur during the calibration cycle of some of the pumps suitable for use with the blood displacing device 50.

Figure 7:
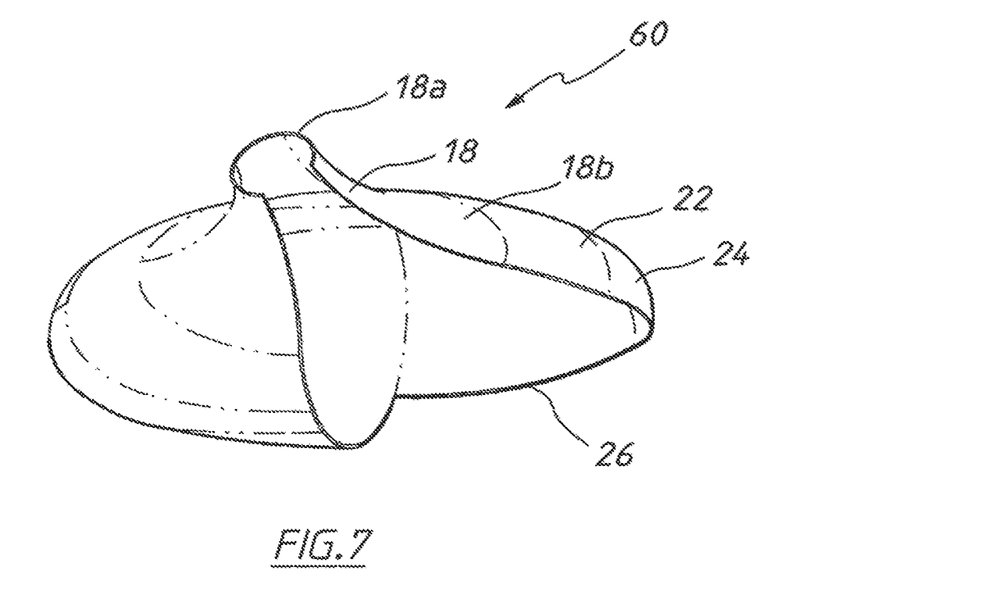
FIG. 7 is a cut away perspective view of a balloon for a third embodiment of an actuator according to the invention.
Figure 8:
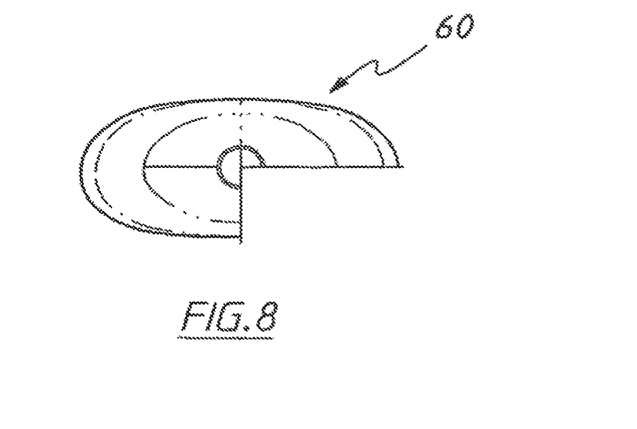
FIG. 8 is a top view of the balloon shown in FIG. 7.

FIGS. 7 and 8 show a balloon 60 for a third embodiment of actuator according to the invention. The balloon 60 is sized for adult use is but is otherwise similar to the first embodiment and like reference numerals are used to indicate like features. When viewed in plan, the first and second body portions 24 and 26 are generally elliptical in shape and have a maximum width and length of 35 mm and 80 mm respectively. The balloon neck portion has a diameter of approximately 10 mm at its distal end 18a and approximately 26-44 mm (oval in cross-section) at its proximal end 18b and a conical converging taper therebetween.

Figure 9:
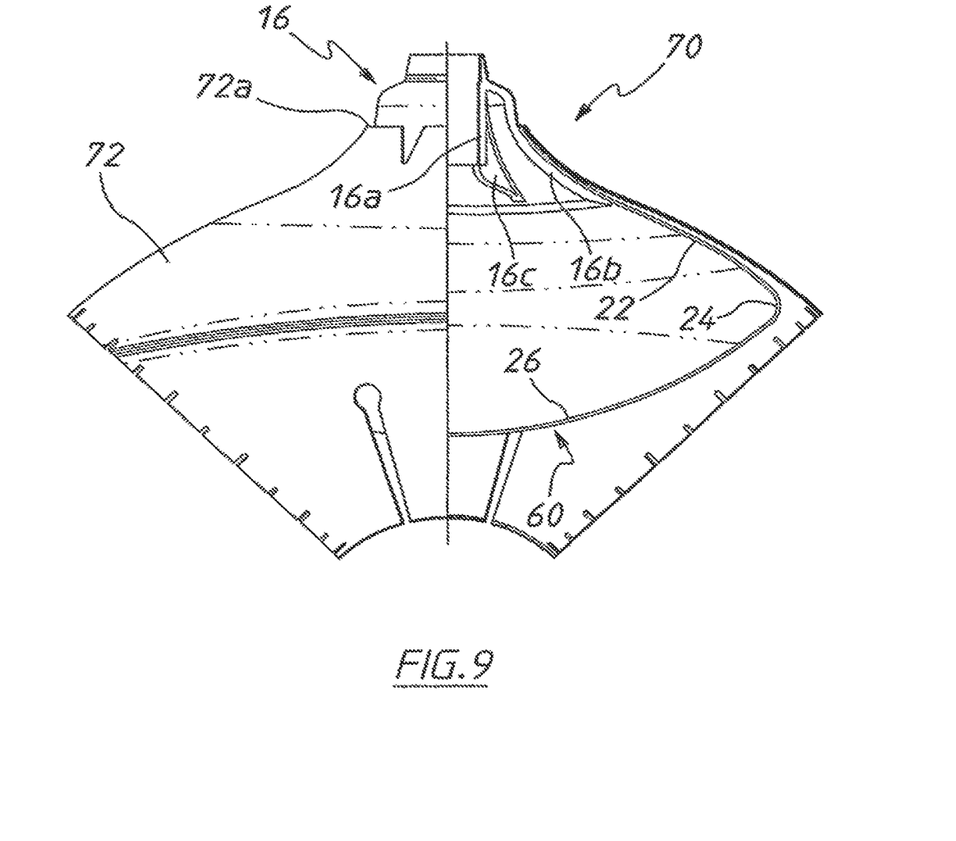
FIG. 9 is a cut away side view of a fourth embodiment of an actuator according to the invention.
Figure 10:
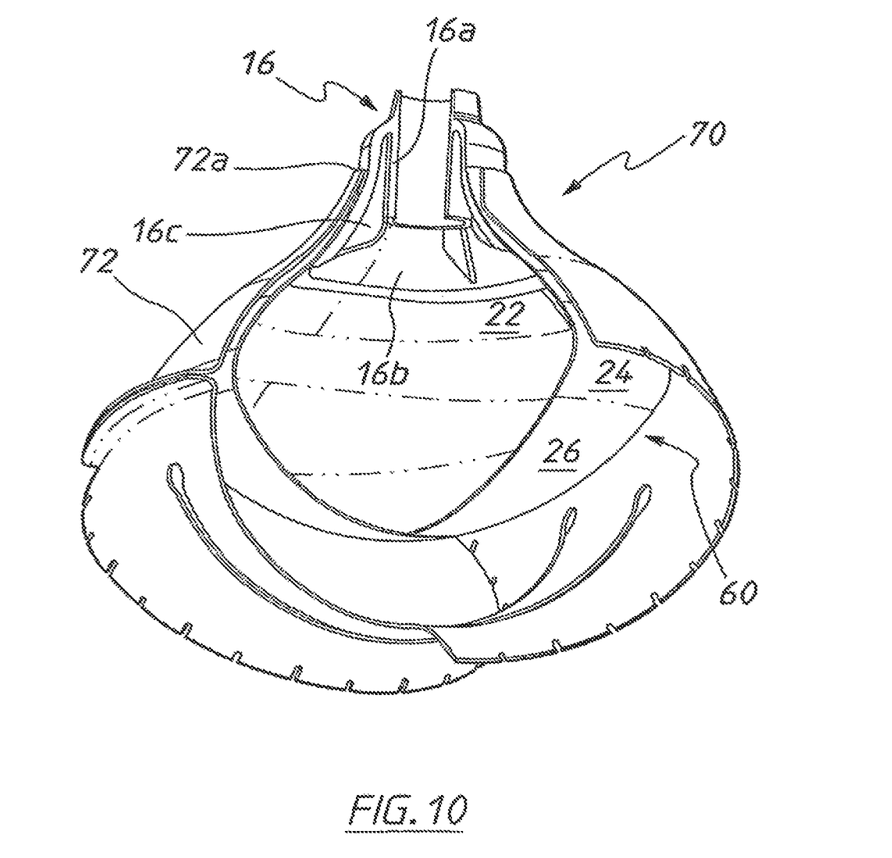
FIG. 10 is a perspective view of the actuator shown in FIG. 9.
Figure 11:
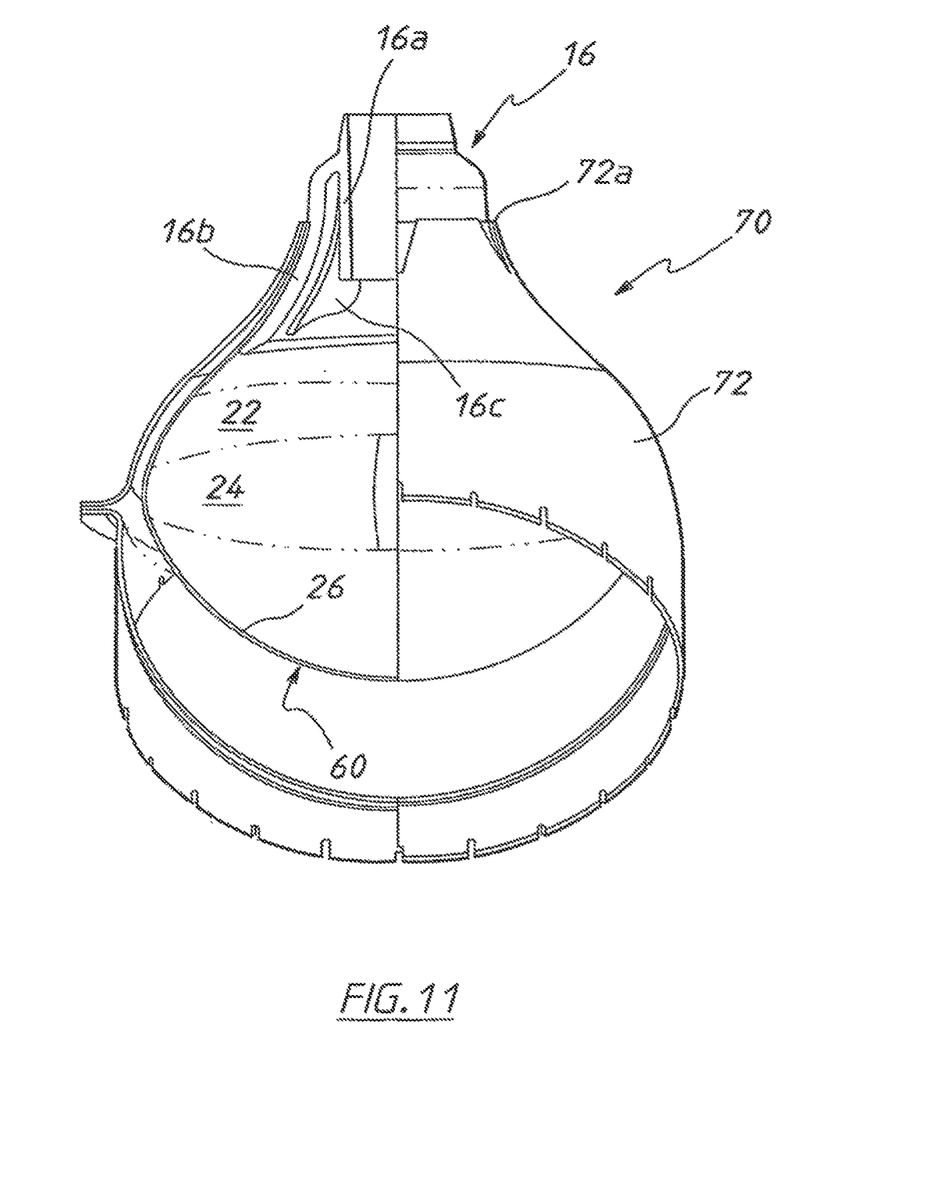
FIG. 11 is a front view of the actuator shown in FIG. 9.

FIGS. 8 to 10 show a fourth embodiment of actuator 70 according to the invention. Like features to earlier embodiments are indicated with like reference numerals. The actuator 70 utilises the balloon 60 shown in FIGS. 7 and 8. The bushing 16 of the actuator 70 differs from earlier embodiments in that it is substantially hollow with a central cylindrical part 16a attached at one end to an outer flared conical part 16b. A series of radial webs 16c are provided between the central cylindrical part 16a and the flared conical part 16b. A flexible, relatively inelastic wrap 72 is provided over the balloon 60, which has an opening 72a through which the bushing 16 protrudes.

It will be appreciated by the persons skilled in the art that numerous variations and/or modifications can be made to the invention as shown in the specific embodiment without departing from the spirit or scope of the invention as broadly defined. For example, the blood displacing devices are described above in relation to extra-aortic counter-pulsation but also suitable for intra aortic counter-pulsation. In the latter the second portion of the balloon replaces a resected portion of arterial vessel, with the opening made in the resected arterial vessel being sealingly connected to the balloon adjacent the flexure region.

What is claimed is:

1. An actuator for a heart assist device, the actuator comprising:
   (a) a restraint component comprising a hole; and
   (b) a flexible balloon comprising:
      (i) a tubular neck portion disposed through the hole in the restraint component;
      (ii) a first body portion coupled to the neck portion, wherein the first body portion is unattachedly disposed adjacent to the restraint component;
      (iii) a second body portion; and
      (iv) a flexure portion coupled to the first body portion and the second body portion,
      wherein the flexible balloon comprises an inflated configuration in which a length of the first body portion is in contact with the restraint component and an deflated configuration in which at least a portion of the length of the first body portion is displaced inwardly away from the restraint component.

2. The actuator of claim 1, wherein the restraint component comprises a shroud or a wrap.

3. The actuator of claim 1, wherein the restraint component comprises a wrap configured to be disposed around the flexible balloon and an exterior of a patient's arterial vessel.

4. The actuator of claim 1, wherein the flexible balloon is formed from silicone, polyurethane, or a polyurethane-polysiloxane block copolymer.

5. The actuator of claim 1, further comprising a bushing disposed within and extending from the tubular neck portion of the flexible balloon, the bushing comprising a bore, wherein the bushing is configured to be coupleable to a fluid line.

6. The actuator of claim 5, wherein the bore comprises at least one internal projection disposed within the bore.

7. The actuator of claim 6, wherein the at least one internal projection comprises at least one flute, at least one rib, or at least one secondary lumen.

8. The actuator of claim 1, wherein the heart assist device is an extra-aortic counterpulsation heart assist device.

9. The actuator of claim 1, wherein the restraint component is disposed against an exterior portion of the tubular neck portion of the flexible balloon, thereby resulting in a snug sealing fit between the restraint component and the tubular neck portion.

10. The actuator of claim 1, wherein the flexure portion has a radius of curvature of at least 0.1 mm in the inflated configuration.

11. The actuator of claim 1, wherein the flexible balloon has a thickness ranging from about 150 microns to about 300 microns.

12. An actuator for a heart assist device, the actuator comprising:
   (a) a flexible balloon comprising:
      (i) a tubular neck portion;
      (ii) a first body portion coupled to the neck portion;
      (iii) a second body portion; and
      (iv) a flexure portion coupled to the first body portion and the second body portion,
      wherein the flexible balloon comprises an inflated configuration in which a length of the first body portion is in contact with the restraint component and an deflated configuration in which at least a portion of the length of the first body portion is displaced inwardly away from the restraint component; and
   (b) a bushing disposed within and extending from the tubular neck portion of the flexible balloon, the bushing comprising a bore, wherein the bushing is configured to be coupleable to an external fluid line.

13. The actuator of claim 12, further comprising a restraint component comprising a hole, wherein the restraint component is a shroud or a wrap.

14. The actuator of claim 13, wherein the restraint component is a wrap configured to be disposed around the flexible balloon and an exterior of a patient's arterial vessel.

15. The actuator of claim 13, wherein the restraint component is disposed against an exterior portion of the tubular neck portion of the balloon, thereby resulting in a snug sealing fit between the restraint component and the tubular neck portion.

16. The actuator of claim 12, wherein the balloon is formed from silicone, polyurethane, or a polyurethane-polysiloxane block copolymer.

17. The actuator of claim 12, wherein the bore comprises at least one internal projection disposed within the bore.

18. The actuator of claim 17, wherein the at least one internal projection comprises at least one flute, at least one rib, or at least one secondary lumen.

19. The actuator of claim 12, wherein the heart assist device is an extra-aortic counterpulsation heart assist device.

\* \* \* \* \*